US012617826B2

(12) United States Patent
Hsieh et al.

(10) Patent No.: US 12,617,826 B2
(45) Date of Patent: May 5, 2026

(54) CLEC2 FUSION PROTEIN AND USES THEREOF

(71) Applicant: Academia Sinica, Taipei City (TW)

(72) Inventors: Shie-Liang Hsieh, Taipei City (TW); Pei-Shan Sung, Taipei City (TW)

(73) Assignee: Academia Sinica, Taipei City (TW)

( * ) Notice: Subject to any disclaimer, the term of this patent is extended or adjusted under 35 U.S.C. 154(b) by 558 days.

(21) Appl. No.: 18/028,747

(22) PCT Filed: Sep. 29, 2021

(86) PCT No.: PCT/US2021/052725
§ 371 (c)(1),
(2) Date: Mar. 27, 2023

(87) PCT Pub. No.: WO2022/072550
PCT Pub. Date: Apr. 7, 2022

(65) Prior Publication Data
US 2023/0365640 A1 Nov. 16, 2023

Related U.S. Application Data

(60) Provisional application No. 63/085,123, filed on Sep. 29, 2020.

(51) Int. Cl.
*C07K 14/47* (2006.01)
*A61P 31/14* (2006.01)
*A61P 31/16* (2006.01)
*A61K 38/00* (2006.01)

(52) U.S. Cl.
CPC .......... *C07K 14/4726* (2013.01); *A61P 31/14* (2018.01); *A61P 31/16* (2018.01); *A61K 38/00* (2013.01); *C07K 2319/02* (2013.01); *C07K 2319/30* (2013.01)

(58) Field of Classification Search
CPC ............ C07K 14/4726; C07K 2319/02; C07K 2319/30; A61P 31/16
See application file for complete search history.

(56) References Cited

FOREIGN PATENT DOCUMENTS

AU 2012271329 A1 * 12/2013 ................ A61P 3/10
WO WO-2021000969 A2 * 1/2021 ............. C12N 15/86

* cited by examiner

*Primary Examiner* — Gyan Chandra
(74) *Attorney, Agent, or Firm* — NZ Carr Law Office

(57) ABSTRACT

Disclosed herein is a CLEC2 fusion protein comprising a first polypeptide and a second polypeptide coupled to the upstream of the first polypeptide. According to embodiments of the present disclosure, the first and the second polypeptides respectively comprise the amino acid sequences of SEQ ID NOs: 1 and 2. Also disclosed therein are uses of the CLEC2 fusion protein in treating severe acute respiratory syndrome coronavirus 2 (SARS-CoV-2) infection and treating influenza virus infection.

7 Claims, 5 Drawing Sheets

Specification includes a Sequence Listing.

```
                    SEQUENCE LISTING

<160> NUMBER OF SEQ ID NOS: 20

<210> SEQ ID NO 1
<211> LENGTH: 179
<212> TYPE: PRT
<213> ORGANISM: Artificial Sequence
<220> FEATURE:
<223> OTHER INFORMATION: synthesized_Extracellular domain of CLEC2

<400> SEQUENCE: 1

Leu Gly Ile Trp Ser Val Met Gln Arg Asn Tyr Leu Gln Gly Glu Asn
1               5                   10                  15

Glu Asn Arg Thr Gly Thr Leu Gln Gln Leu Ala Lys Arg Phe Cys Gln
            20                  25                  30

Tyr Val Val Lys Gln Ser Glu Leu Lys Gly Thr Phe Lys Gly His Lys
        35                  40                  45

Cys Ser Pro Cys Asp Thr Asn Trp Arg Tyr Tyr Gly Asp Ser Cys Tyr
```

-continued

```
        50              55              60

Gly Phe Phe Arg His Asn Leu Thr Trp Glu Glu Ser Lys Gln Tyr Cys
65              70              75              80

Thr Asp Met Asn Ala Thr Leu Leu Lys Ile Asp Asn Arg Asn Ile Val
                85              90              95

Glu Tyr Ile Lys Ala Arg Thr His Leu Ile Arg Trp Val Gly Leu Ser
            100             105             110

Arg Gln Lys Ser Asn Glu Val Trp Lys Trp Glu Asp Gly Ser Val Ile
        115             120             125

Ser Glu Asn Met Phe Glu Phe Leu Glu Asp Gly Lys Gly Asn Met Asn
    130             135             140

Cys Ala Tyr Phe His Asn Gly Lys Met His Pro Thr Phe Cys Glu Asn
145             150             155             160

Lys His Tyr Leu Met Cys Glu Arg Lys Ala Gly Met Thr Lys Val Asp
            165             170             175

Gln Leu Pro

<210> SEQ ID NO 2
<211> LENGTH: 227
<212> TYPE: PRT
<213> ORGANISM: Artificial Sequence
<220> FEATURE:
<223> OTHER INFORMATION: synthesized_Fc domain

<400> SEQUENCE: 2

Asp Lys Thr His Thr Cys Pro Pro Cys Pro Ala Pro Glu Leu Leu Gly
1               5               10              15

Gly Pro Ser Val Phe Leu Phe Pro Pro Lys Pro Lys Asp Thr Leu Met
                20              25              30

Ile Ser Arg Thr Pro Glu Val Thr Cys Val Val Val Asp Val Ser His
            35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
                85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
        115             120             125

Tyr Thr Leu Pro Pro Ser Arg Asp Glu Leu Thr Lys Asn Gln Val Ser
    130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
                165             170             175

Val Leu Asp Ser Asp Gly Ser Phe Phe Leu Tyr Ser Lys Leu Thr Val
                180             185             190

Asp Lys Ser Arg Trp Gln Gln Gly Asn Val Phe Ser Cys Ser Val Met
            195             200             205

His Glu Ala Leu His Asn His Tyr Thr Gln Lys Ser Leu Ser Leu Ser
    210             215             220

Pro Gly Lys
225
```

-continued

```
<210> SEQ ID NO 3
<211> LENGTH: 22
<212> TYPE: PRT
<213> ORGANISM: Artificial Sequence
<220> FEATURE:
<223> OTHER INFORMATION: synthesized_signal peptide

<400> SEQUENCE: 3

Met Asp Met Arg Val Pro Ala Gln Leu Leu Gly Leu Leu Leu Trp
1               5                   10                  15

Leu Pro Gly Ala Arg Cys
            20

<210> SEQ ID NO 4
<211> LENGTH: 19
<212> TYPE: PRT
<213> ORGANISM: Artificial Sequence
<220> FEATURE:
<223> OTHER INFORMATION: synthesized_signal peptide

<400> SEQUENCE: 4

Met Glu Trp Ser Trp Val Phe Leu Phe Phe Leu Ser Val Thr Thr Gly
1               5                   10                  15

Val His Ser

<210> SEQ ID NO 5
<211> LENGTH: 5
<212> TYPE: PRT
<213> ORGANISM: Artificial Sequence
<220> FEATURE:
<223> OTHER INFORMATION: synthesized_linker

<400> SEQUENCE: 5

Gly Gly Gly Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: synthesized_linker

<400> SEQUENCE: 6

Glu Pro Lys Ser Ser
1               5

<210> SEQ ID NO 7
<211> LENGTH: 11
<212> TYPE: PRT
<213> ORGANISM: Artificial Sequence
<220> FEATURE:
<223> OTHER INFORMATION: synthesized_linker

<400> SEQUENCE: 7

Gly Gly Gly Gly Ser Gly Gly Gly Gly Ala Ser
1               5                   10

<210> SEQ ID NO 8
<211> LENGTH: 436
<212> TYPE: PRT
<213> ORGANISM: Artificial Sequence
<220> FEATURE:
<223> OTHER INFORMATION: synthesized_CLEC2.Fc fusion protein
```

-continued

<400> SEQUENCE: 8

```
Met Glu Trp Ser Trp Val Phe Leu Phe Phe Leu Ser Val Thr Thr Gly
1               5                   10                  15

Val His Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
        50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
        130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
            165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
        210                 215                 220

Ser Val Met His Glu Ala Leu His Asn His Tyr Thr Gln Lys Ser Leu
225                 230                 235                 240

Ser Leu Ser Pro Gly Lys Gly Gly Gly Ser Gly Gly Gly Gly Ala
            245                 250                 255

Ser Leu Gly Ile Trp Ser Val Met Gln Arg Asn Tyr Leu Gln Gly Glu
            260                 265                 270

Asn Glu Asn Arg Thr Gly Thr Leu Gln Gln Leu Ala Lys Arg Phe Cys
            275                 280                 285

Gln Tyr Val Val Lys Gln Ser Glu Leu Lys Gly Thr Phe Lys Gly His
        290                 295                 300

Lys Cys Ser Pro Cys Asp Thr Asn Trp Arg Tyr Tyr Gly Asp Ser Cys
305                 310                 315                 320

Tyr Gly Phe Phe Arg His Asn Leu Thr Trp Glu Glu Ser Lys Gln Tyr
            325                 330                 335

Cys Thr Asp Met Asn Ala Thr Leu Leu Lys Ile Asp Asn Arg Asn Ile
            340                 345                 350

Val Glu Tyr Ile Lys Ala Arg Thr His Leu Ile Arg Trp Val Gly Leu
            355                 360                 365

Ser Arg Gln Lys Ser Asn Glu Val Trp Lys Trp Glu Asp Gly Ser Val
        370                 375                 380

Ile Ser Glu Asn Met Phe Glu Phe Leu Glu Asp Gly Lys Gly Asn Met
385                 390                 395                 400

Asn Cys Ala Tyr Phe His Asn Gly Lys Met His Pro Thr Phe Cys Glu
            405                 410                 415
```

-continued

```
Asn Lys His Tyr Leu Met Cys Glu Arg Lys Ala Gly Met Thr Lys Val
            420                 425                 430

Asp Gln Leu Pro
        435

<210> SEQ ID NO 9
<211> LENGTH: 6
<212> TYPE: PRT
<213> ORGANISM: Artificial Sequence
<220> FEATURE:
<223> OTHER INFORMATION: synthesized_linker

<400> SEQUENCE: 9

Gly Gly Pro Gly Gly Pro
1               5

<210> SEQ ID NO 10
<211> LENGTH: 9
<212> TYPE: PRT
<213> ORGANISM: Artificial Sequence
<220> FEATURE:
<223> OTHER INFORMATION: synthesized_linker

<400> SEQUENCE: 10

Gly Gly Pro Gly Gly Pro Gly Gly Pro
1               5

<210> SEQ ID NO 11
<211> LENGTH: 12
<212> TYPE: PRT
<213> ORGANISM: Artificial Sequence
<220> FEATURE:
<223> OTHER INFORMATION: synthesized_linker

<400> SEQUENCE: 11

Gly Gly Pro Gly Gly Pro Gly Gly Pro Gly Gly Pro
1               5                   10

<210> SEQ ID NO 12
<211> LENGTH: 15
<212> TYPE: PRT
<213> ORGANISM: Artificial Sequence
<220> FEATURE:
<223> OTHER INFORMATION: synthesized_linker

<400> SEQUENCE: 12

Gly Gly Pro Gly Gly Pro Gly Gly Pro Gly Gly Pro Gly Gly Pro
1               5                   10                  15

<210> SEQ ID NO 13
<211> LENGTH: 10
<212> TYPE: PRT
<213> ORGANISM: Artificial Sequence
<220> FEATURE:
<223> OTHER INFORMATION: synthesized_linker

<400> SEQUENCE: 13

Gly Gly Gly Gly Ser Gly Gly Gly Gly Ser
1               5                   10

<210> SEQ ID NO 14
<211> LENGTH: 15
<212> TYPE: PRT
<213> ORGANISM: Artificial Sequence
<220> FEATURE:
<223> OTHER INFORMATION: synthesized_linker
```

-continued

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 20
<212> TYPE: PRT
<213> ORGANISM: Artificial Sequence
<220> FEATURE:
<223> OTHER INFORMATION: synthesized_linker

<400> SEQUENCE: 15

Gly Gly Gly Gly Ser Gly Gly Gly Gly Ser Gly Gly Gly Gly Ser Gly
1               5                   10                  15

Gly Gly Gly Ser
            20

<210> SEQ ID NO 16
<211> LENGTH: 25
<212> TYPE: PRT
<213> ORGANISM: Artificial Sequence
<220> FEATURE:
<223> OTHER INFORMATION: synthesized_linker

<400> SEQUENCE: 16

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 17
<211> LENGTH: 1308
<212> TYPE: DNA
<213> ORGANISM: Artificial Sequence
<220> FEATURE:
<223> OTHER INFORMATION: synthesized_DNA encoding CLEC2.Fc

<400> SEQUENCE: 17
atggaatgga gctgggtctt tctcttcttc ctgtcagtaa ctacaggtgt ccactccgac      60
aaaactcaca catgcccacc gtgcccagca cctgaactcc tggggggacc gtcagtcttc     120
ctcttccccc caaaacccaa ggacaccctc atgatctccc ggacccctga ggtcacatgc     180
gtggtggtgg acgtgagcca cgaagaccct gaggtcaagt tcaactggta cgtggacggc     240
gtggaggtgc ataatgccaa gacaaagccg cgggaggagc agtacaacag cacgtaccgt     300
gtggtcagcg tcctcaccgt cctgcaccag gactggctga atggcaagga gtacaagtgc     360
aaggtctcca acaaagccct cccagccccc atcgagaaaa ccatctccaa agccaaaggg     420
cagccccgag agccacaggt gtacaccctg cccccatccc gggatgagct gaccaagaac     480
caggtcagcc tgacctgcct ggtcaaaggc ttctatccca gcgacatcgc cgtggagtgg     540
gagagcaatg ggcagccgga gaacaactac aagaccacgc ctcccgtgct ggactccgac     600
ggctccttct tcctctacag caagctcacc gtggacaaga gcaggtggca gcaggggaac     660
gtcttctcat gctccgtgat gcatgaggct ctgcacaacc actacacgca gaagagcctc     720
tccctgtctc cgggtaaagg aggcggtgga tctggcggag gtggagctag cgggatttgg     780
tctgtcatgc agcgcaatta cctacaaggt gagaatgaaa tcgcacagg aactctgcaa     840 caattagcaa agcgcttctg tcaatatgtg gtaaacaat cagaactaaa gggcactttc     900
aaaggtcata atgcagccc ctgtgacaca aactggagat attatggaga tagctgctat     960

-continued

```
gggttcttca ggcacaactt aacatgggaa gagagtaagc agtactgcac tgacatgaat      1020
gctactctcc tgaagattga caaccggaac attgtggagt acatcaaagc caggactcat      1080
ttaattcgtt gggtcggatt atctcgccag aagtcgaatg aggtctggaa gtgggaggat      1140
ggctcggtta tctcagaaaa tatgtttgag tttttggaag atggaaaagg aaatatgaat      1200
tgtgcttatt ttcataatgg gaaaatgcac cctaccttct gtgagaacaa acattattta      1260
atgtgtgaga ggaaggctgg catgaccaag gtggaccaac taccttaa                   1308
```

```
<210> SEQ ID NO 18
<211> LENGTH: 1255
<212> TYPE: PRT
<213> ORGANISM: Artificial Sequence
<220> FEATURE:
<223> OTHER INFORMATION: synthesized_SARS-CoV-2 spike protein

<400> SEQUENCE: 18

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300
```

-continued

```
Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
                340                 345                 350

Ser Val Leu Tyr Asn Ser Thr Phe Phe Ser Thr Phe Lys Cys Tyr Gly
                355                 360                 365

Val Ser Ala Thr Lys Leu Asn Asp Leu Cys Phe Ser Asn Val Tyr Ala
                370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                    405                 410                 415

Met Gly Cys Val Leu Ala Trp Asn Thr Arg Asn Ile Asp Ala Thr Ser
                420                 425                 430

Thr Gly Asn Tyr Asn Tyr Lys Tyr Arg Tyr Leu Arg His Gly Lys Leu
                435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
                500                 505                 510

Pro Lys Leu Ser Thr Asp Leu Ile Lys Asn Gln Cys Val Asn Phe Asn
                515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
                580                 585                 590

Glu Val Ala Val Leu Tyr Gln Asp Val Asn Cys Thr Asp Val Ser Thr
                595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
                660                 665                 670

Ser Ile Val Ala Tyr Thr Met Ser Leu Gly Ala Asp Ser Ser Ile Ala
                675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720
```

-continued

```
Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
        770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
            805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
        850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
            885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
        930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
            965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
            995                 1000                1005

Thr Lys Met Ser Glu Cys Val Leu Gly Gln Ser Lys Arg Val Asp Phe
    1010                1015                1020

Cys Gly Lys Gly Tyr His Leu Met Ser Phe Pro Gln Ala Ala Pro His
1025                1030                1035                1040

Gly Val Val Phe Leu His Val Thr Tyr Val Pro Ser Gln Glu Arg Asn
            1045                1050                1055

Phe Thr Thr Ala Pro Ala Ile Cys His Glu Gly Lys Ala Tyr Phe Pro
            1060                1065                1070

Arg Glu Gly Val Phe Val Phe Asn Gly Thr Ser Trp Phe Ile Thr Gln
            1075                1080                1085

Arg Asn Phe Phe Ser Pro Gln Ile Ile Thr Thr Asp Asn Thr Phe Val
        1090                1095                1100

Ser Gly Asn Cys Asp Val Val Ile Gly Ile Ile Asn Asn Thr Val Tyr
1105                1110                1115                1120

Asp Pro Leu Gln Pro Glu Leu Asp Ser Phe Lys Glu Glu Leu Asp Lys
            1125                1130                1135

Tyr Phe Lys Asn His Thr Ser Pro Asp Val Asp Leu Gly Asp Ile Ser
```

-continued

```
                1140                1145                1150

Gly Ile Asn Ala Ser Val Val Asn Ile Gln Lys Glu Ile Asp Arg Leu
        1155                1160                1165

Asn Glu Val Ala Lys Asn Leu Asn Glu Ser Leu Ile Asp Leu Gln Glu
    1170                1175                1180

Leu Gly Lys Tyr Glu Gln Tyr Ile Lys Trp Pro Trp Tyr Val Trp Leu
1185                1190                1195                1200

Gly Phe Ile Ala Gly Leu Ile Ala Ile Val Met Val Thr Ile Leu Leu
                1205                1210                1215

Cys Cys Met Thr Ser Cys Cys Ser Cys Leu Lys Gly Ala Cys Ser Cys
                1220                1225                1230

Gly Ser Cys Cys Lys Phe Asp Glu Asp Asp Ser Glu Pro Val Leu Lys
        1235                1240                1245

Gly Val Lys Leu His Tyr Thr
    1250                1255

<210> SEQ ID NO 19
<211> LENGTH: 222
<212> TYPE: PRT
<213> ORGANISM: Artificial Sequence
<220> FEATURE:
<223> OTHER INFORMATION: synthesized_receptor binding domain

<400> SEQUENCE: 19

Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Lys Ile Ser Asn Cys Val Ala Asp Tyr Ser
        35                  40                  45

Val Leu Tyr Asn Ser Thr Phe Phe Ser Thr Phe Lys Cys Tyr Gly Val
    50                  55                  60

Ser Ala Thr Lys Leu Asn Asp Leu Cys Phe Ser Asn Val Tyr Ala Asp
65                  70                  75                  80

Ser Phe Val Val Lys Gly Asp Asp Val Arg Gln Ile Ala Pro Gly Gln
                85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
        115                 120                 125

Gly Asn Tyr Asn Tyr Lys Tyr Arg Tyr Leu Arg His Gly Lys Leu Arg
    130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
            165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp Leu Ile Lys Asn Gln Cys Val Asn Phe
    210                 215                 220

<210> SEQ ID NO 20
<211> LENGTH: 71
<212> TYPE: PRT
```

-continued

```
<213> ORGANISM: Artificial Sequence
<220> FEATURE:
<223> OTHER INFORMATION: synthesized_ACE2 binding motif

<400> SEQUENCE: 20

Asn Thr Arg Asn Ile Asp Ala Thr Ser Thr Gly Asn Tyr Asn Tyr Lys
1               5                   10                  15

Tyr Arg Tyr Leu Arg His Gly Lys Leu Arg Pro Phe Glu Arg Asp Ile
            20                  25                  30

Ser Asn Val Pro Phe Ser Pro Asp Gly Lys Pro Cys Thr Pro Pro Ala
        35                  40                  45

Leu Asn Cys Tyr Trp Pro Leu Asn Asp Tyr Gly Phe Tyr Thr Thr Thr
    50                  55                  60

Gly Ile Gly Tyr Gln Pro Tyr
65                  70
```

CLEC2 FUSION PROTEIN AND USES THEREOF

CROSS REFERENCE TO RELATED APPLICATION

This application is a U.S. National Stage Filing under 35 U.S.C. 371 from International Patent Application Serial No. PCT/US21/52725, filed Sep. 29, 2021, and published on Apr. 7, 2022, which claims the priority of U.S. Ser. No. U.S. 63/085,123, filed Sep. 29, 2020, the disclosure of which are incorporated by reference herein in their entireties.

BACKGROUND OF THE INVENTION

1. Field of the Invention

The present disclosure in general relates to the field of disease treatment. More particularly, the present disclosure relates to a CLEC2 fusion protein, and the treatment of severe acute respiratory syndrome coronavirus 2 (SARS-CoV-2) infection or influenza virus infection by using the CLEC2 fusion protein.

2. Description of Related Art

SARS-CoV-2 is the etiological agent of the coronavirus-induced disease 19 (COVID-19). Similar to SARS-CoV, SARS-CoV-2 binds angiotensin converting enzyme 2 (ACE2) via the receptor-binding domain of Spike protein (SARS-CoV-2 RBD) for cellular entry. Due to extensive infiltration of neutrophils and macrophages in lung, COVID-19 patients suffer from acute respiratory distress syndrome (ARDS), which causes acute lung injury and fibrosis. These COVID-19 patients often have severe pulmonary inflammation with thrombotic complications, such as microangiopathy, pulmonary embolism and cerebral infarction. An extremely high incidence of thromboemboli in COVID-19 patients is one of the most obvious post-mortem findings.

Even though the pathogenesis of thromboemboli formation in COVID-19 is unclear, a recent study indicates that excessive production of neutrophil extracellular traps (NETS) are associated with thromboemboli formation in human diseases. It has been shown that elevated levels of cell-free DNA, myeloperoxidase and citrullinated histone 3 were noted in the sera of COVID-19 patients and correlated with disease severity. Moreover, sera from COVID-19 patients trigger NET formation in neutrophils isolated from healthy controls. All the evidence suggests that NET formation may contribute to the severe intravascular coagulopathy in COVID-19 patients, and targeting excessive NET formation may reduce thrombosis and the clinical severity of COVID-19 in patients. However, the mechanism of SARS-CoV-2-induced NET formation is still unknown.

Even with the advances made in the last several months of the COVID-19 pandemic, there is still no treatment for COVID-19. Accordingly, there is still an interest in developing a method for treating the infection of SARS-CoV-2 thereby improving the life span and quality of COVID-19 patients.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based on unexpected discovery that CLEC2 (also termed "CLEC-1B", a Syk-coupled C-type lectin in platelets) specifically interacts with the receptor binding domain (RBD) of SARS-CoV-2 spike protein (i.e., SARS-CoV-2 RBD), and the blockade of CLEC2 inhibits SARS-CoV-2/platelet-induced NET formation. Accordingly, CLEC2 may serve as a new therapeutic target for the treatment or prophylaxis of SARS-CoV-2 infection.

The first aspect of the present disclosure is thus directed to a fusion protein comprising a first polypeptide, and a second polypeptide coupled to the first polypeptide. According to embodiments of the preset disclosure, the first polypeptide is an extracellular domain of CLEC2 and comprises the amino acid sequence of SEQ ID NO: 1, and the second polypeptide is a fragment crystallizable (Fc) region of immunoglobulin and comprises the amino acid sequence of SEQ ID NO: 2. In structure, the second polypeptide (i.e., the Fc region of immunoglobulin) is disposed at and connected to the upstream of the first polypeptide (i.e., the extracellular domain of CLEC2).

Optionally, the present fusion protein further comprises a signal peptide disposed at and connected to the upstream of the second polypeptide. According to one embodiment, the signal peptide comprises the amino acid sequence of SEQ ID NO: 3. According to another embodiment, the signal peptide comprises the amino acid sequence of SEQ ID NO: 4.

Optionally, the present fusion protein further comprises a linker disposed between the first and the second polypeptides. According to some embodiments of the present disclosure, the linker comprises the amino acid sequence of $(GGP)_{1-5}$, the amino acid sequence of SEQ ID NO: 5, or the amino acid sequence of SEQ ID NO: 6. In one specific embodiment, the linker comprises the amino acid sequence of SEQ ID NO: 7.

According to one preferred embodiment, the present fusion protein comprises the amino acid sequence of SEQ ID NO: 8.

The second aspect of the present disclosure pertains to a method of treating the infection of SARS-CoV-2 in a subject. The method comprises administering to the subject an effective amount of the fusion protein of the present disclosure thereby alleviating or ameliorating the symptom associated with SARS-CoV-2 infection.

According to certain embodiments of the present disclosure, the subject is a human, in which the effective amount is 10 µg/kg to 10 mg/kg body weight of the subject. Preferably, the present fusion protein is administered to the subject in an amount of 0.1 mg/kg to 1 mg/kg body weight of the subject.

Also disclosure herein is a method of treating the infection of influenza virus in a subject. The method comprises administering to the subject an effective amount of the fusion protein of the present disclosure thereby alleviating or ameliorating the symptom associated with influenza virus infection.

According to certain embodiments of the present disclosure, the subject is a human, in which the effective amount is 10 µg/kg to 10 mg/kg body weight of the subject. Preferably, the present fusion protein is administered to the subject in an amount of 0.1 mg/kg to 1 mg/kg body weight of the subject.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 1A: the interaction between specified human C-type lectins and recombinant SARS-CoV-2 RBD was determined by ELISA. HC_serum: serum from healthy controls; COVID-19-serum: serum from COVID-19 patients. FIG. 1B: human neutrophils were incubated with SARS-CoV-2 (MOI=0.1 or 1) in the presence of isotype control (human IgG1, hIgG1) or human CLEC2.Fc protein with or without autologous platelets (PLTs) at 37° C. for 5 hours. The NET formation structures were visualized by fluorescent staining of DNA, histone, and myeloperoxidase (MPO). The level of NET was calculated by area of histone ($\mu m^2$). Data are mean±sd and repeats of at least three independent experiments. *$p<0.05$, $p<0.01$, *$p<0.001$, ****$p<0.0001$ (Student's t-test).

FIG. 2A: the MPO-positive area in the lung tissues of mice administered with specified treatments. FIG. 2B: the CD42b-positive area in the lung tissues of mice administered with specified treatments. FIG. 2C: the area of collagen deposition in the lung tissues of mice administered with specified treatments. Data are mean±sd and repeats of at least three independent experiments. *$p<0.05$, *$p<0.001$, **$p<0.0001$ (Student's t-test). d.p.i.: day post-infection.

FIG. 4A: weight changes of H5N1-challenged mice pretreated with hIgG1 or CLEC2.Fc protein. FIG. 4B: survival rates of H5N1-challenged mice pretreated with hIgG1 or CLEC2.Fc protein. N=9 per group.

DETAILED DESCRIPTION OF THE INVENTION

Figure 1A:
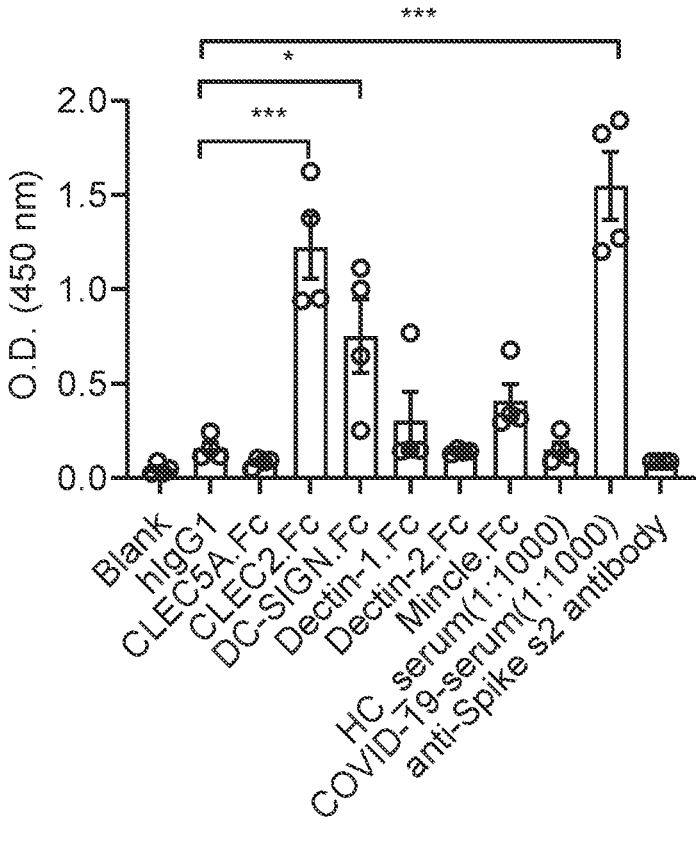
FIGS. 1A and 1B are histograms respectively depicting the effect of CLEC2.Fc protein on SARS-CoV-2-induced NET formation according to Example 1 of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "fusion protein" herein refers to a combination of two proteins or peptides joined in any manner or by any type of linkage, covalent, electrostatic, hydrophobic-interaction, affinity-type, or otherwise, that maintains the linkage between the partners, prevents cleavage of the linkage during the procedural steps that are followed in the practice of this invention, and leaves the binding characteristics of the protein substantially unchanged. A preferred kind of fusion protein for the purpose of this invention is a peptide made from a recombinant gene that contains portions of two or more different genes, the genes being joined with or without a linker sequence so that their coding sequences are in the same reading frame, i.e., so that the genetic apparatus reads the gene fusion as a single gene. This type of fusion protein is also known as a hybrid protein or a chimeric protein.

As used herein, the term "extracellular domain" when used in reference to a membrane bound protein refers to the portion of the protein that is exposed on the extracellular side of a lipid bilayer of a cell. Specifically, the term "extracellular domain" of CLEC2 is well-known in the art, and refers to the region of the CLEC2 sequence that extends into the extracellular environment (i.e., the environment outside a cell).

The terms "Fc region" and "fragment crystallizable region" are used interchangeably herein and refer to a C-terminal region of an immunoglobulin (e.g., IgG1, IgG2, IgG3, IgG4, IgA1, IgA2, IgD, IgE, or IgM) heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region may also include any portion of a hinge region (e.g., a native or modified hinge region). The Fc can be of any mammal, including human, and may be post-translationally modified (e.g., by glycosylation). In a non-limiting example, the Fc region is the region of human IgG1 and has the amino acid sequence of SEQ ID NO: 2.

As discussed herein, minor variations in the amino acid sequences of polypeptides (i.e., the fusion protein of the present disclosure) are contemplated as being encompassed by the presently disclosed and claimed inventive concept(s), providing that the variations in the amino acid sequence maintain at least 85% sequence identity, such as at least 85%, 86%, 87%, 88%, 89%, 90%, 91%, 92%, 93%, 94%, 95%, 96%, 97%, 98% and 99% sequence identity. Polypeptides of the present disclosure may be modified specifically to alter a feature of the peptide unrelated to its physiological activity. For example, certain amino acids can be changed and/or deleted without affecting the binding activity of the polypeptide in this study (i.e., the binding affinity to SARS-CoV-2 RBD, and/or the inhibitory effect on influenza virus). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of proteins/peptides can be readily prepared by those of ordinary skill in the art. Preferred amino- and carboxy-termini of fragments or analogs occur near boundaries of functional domains.

"Percentage (%) sequence identity" is defined as the percentage of amino acid residues in a candidate sequence that are identical with the amino acid residues in the specific peptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100$$

where X is the number of amino acid residues scored as identical matches by the sequence alignment program BLAST in that program's alignment of A and B, and where Y is the total number of amino acid residues in A or B, whichever is shorter.

As used herein, the term "treat", "treating" and "treatment" are interchangeable, and encompasses partially or completely preventing, ameliorating, mitigating and/or managing a symptom, a secondary disorder or a condition associated with SARS-CoV-2 infection or influenza virus infection. The term "treating" as used herein refers to application or administration of the fusion protein of the present disclosure to a subject, who has a symptom, a secondary disorder or a condition associated with SARS-CoV-2 infection or influenza virus infection, with the purpose to partially or completely alleviate, ameliorate, relieve, delay onset of, inhibit progression of, reduce severity of, and/or reduce incidence of one or more symptoms, secondary disorders or features associated with SARS-CoV-2 infection or influenza virus infection. Symptoms, secondary disorders, and/or conditions associated with SARS-CoV-2 infection include, but are not limited to, acute respiratory distress syndrome (ARDS), pulmonary inflammation, pulmonary collagen deposition, lung injury, lung fibrosis, immunothrombosis, immune cell infiltration (e.g., the infiltration of monocytes, neutrophils and/or T cells), intravascular coagulopathy, microangiopathy, pulmonary embolism, cerebral infarction, and a combination thereof. Symptoms, secondary disorders, and/or conditions associated with influenza virus infection include, but are not limited to, fever, cough, sore throat, runny or stuffy nose, muscle or body aches, headaches, fatigue, vomiting, diarrhea, pulmonary inflammation, weight loss, and a combination thereof. Treatment may be administered to a subject who exhibits only early signs of such symptoms, disorder, and/or condition for the purpose of decreasing the risk of developing the symptoms, secondary disorders, and/or conditions associated with SARS-CoV-2 infection or influenza virus infection. Treatment is generally "effective" if one or more symptoms or clinical markers are reduced as that term is defined herein. Alternatively, a treatment is "effective" if the progression of a symptom, disorder or condition is reduced or halted.

The term "administered", "administering" or "administration" are used interchangeably herein to refer a mode of delivery, including, without limitation, intravenously, intramuscularly, intraperitoneally, intraarterially, intracranially, or subcutaneously deliver an agent (e.g., a CLEC2 fusion protein) of the present invention.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the CLEC2 fusion protein of the present disclosure), such as molar concentration, mass concentration, volume concentration, molality, mole fraction, mass fraction and mixing ratio. Persons having ordinary skills could calculate the human equivalent dose (HED) for the medicament (such as the CLEC2 fusion protein of the present disclosure) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" or "patient" refers to a mammal including the human species that is treatable with CLEC2 fusion protein and/or methods of the present invention. The term "subject" is intended to refer to both the male and female gender unless one gender is specifically indicated.

II. Description of the Invention

COVID-19 affects more than fifteen million patients worldwide, and most people die of acute respiratory distress syndrome. Recent studies indicated that excessive neutrophil extracellular traps (NETs) contribute to immunothrombosis, thereby leading to extensive intravascular coagulopathy and multiple organ dysfunction. Autopsy of COVID-19 patients demonstrated the presence of thrombosis and microangiopathy in the small vessels and capillaries. Understanding the mechanism of SARS-CoV-2-induced NETosis (cell death by NETs) is critical to reduce thrombosis and prevent visceral organ infarction. The inventor of the present disclosure discovered that CLEC2 specifically interacts with SARS-CoV-2 RBD, in which SARS-CoV-2 induces intense NET formation in the presence of platelets, and the blockade of CLEC2 abolishes SARS-CoV-2-induced NET formation. These results suggest that CLEC2 on platelets plays a critical role in SARS-CoV-2-induced immunothrombosis, and the blockade of CLEC2 is therapeutically promising for inhibiting SARS-CoV-2-induced intravascular coagulopathy and may be beneficial to COVID-19 patients.

(II-1) CLEC2 Fusion Protein (CLEC2.Fc Protein)

The first aspect of the present disclosure is directed to a CLEC2 fusion protein (hereinafter, as "CLEC2.Fc protein"), which comprises an extracellular domain of CLEC2 (as the first polypeptide), and a fragment crystallizable (Fc) region (as the second polypeptide) coupled to the extracellular domain of CLEC2. Depending on desired purposes, the Fc region may be disposed at the upstream or downstream of the extracellular domain of CLEC2. According to certain preferred embodiments, the Fc region is disposed at and connected to the upstream of the extracellular domain of CLEC2.

According to embodiments of the present disclosure, the extracellular domain of the CLEC2.Fc protein comprises an amino acid sequence at least 85% identical to SEQ ID NO: 1; preferably, at least 90% identical to SEQ ID NO: 1; more preferably, at least 95% identical to SEQ ID NO: 1. In one specific example, the extracellular domain of the present CLEC2.Fc protein comprises the amino acid sequence 100% identical to SEQ ID NO: 1.

Regarding the Fc region of the present CLEC2.Fc protein, it is derived from a human immunoglobulin (e.g., IgG1, IgG2, IgG3, IgG4, IgA1, IgA2, IgD, IgE, or IgM). Preferably, the Fc region of the CLEC2.Fc protein is derived from human IgG1, and comprises an amino acid sequence at least 85% identical to SEQ ID NO: 2. As would be appreciated, the amino acid sequence of the Fc region may vary (e.g., being substituted by conserved or non-conserved amino acid residues) without affecting its desired function, such as stabilizing the function and/or prolonging the half-life of the protein coupled therewith (e.g., the extracellular domain of CLEC2 of the present CLEC2.Fc protein). According to some preferred embodiments, the Fc region comprises an amino acid sequence at least 90% identical to SEQ ID NO: 2. More preferably, the Fc region comprises an amino acid sequence at least 95% identical to SEQ ID NO: 2. In one working example of the present disclosure, the Fc region comprises the amino acid sequence 100% identical to SEQ ID NO: 2.

For the purpose of stabilizing the function and/or prolonging the half-life of the extracellular domain of CLEC2, the Fc region may alternatively be replaced by other molecules with stabilizing properties, such as albumin (e.g., human serum albumin), albumin binding domain, transferrin, polyethylene glycol (PEG), recombinant PEG, homo-amino acid polymer (HAP), elastin-liked peptide (ELP), carboxy-terminal peptide (CTP), and gelatin-like protein (GLK).

Optionally, the Fc region is coupled to the extracellular domain of CLEC2 via a linker, which, according to some embodiments of the present disclosure, may be a cleavable or a non-cleavable linker. Optionally, the linker may be a flexible linker or an inflexible linker. The linker should be a length sufficiently long to allow the extracellular domain of CLEC2 and the Fc region to be linked without steric hindrance from one another and sufficiently short to retain the intended activity of the fusion protein. The linker preferably is sufficiently hydrophilic to avoid or minimize instability of the fusion protein. The linker preferably is sufficiently hydrophilic to avoid or minimize insolubility of the fusion protein. The linker should be sufficiently stable in vivo (e.g., it is not cleaved by serum, enzymes, etc.) to permit the fusion protein to be operative in vivo. Preferably, the linker consists of amino acid residues of glutamine (Q), serine (S), glycine (G), glutamate (E), proline (P), histidine (H) and/or arginine (R). More preferably, the linker consists of serine (S), glycine (G) and/or proline (P). In certain embodiments, the linker is a peptide containing 1-25 amino acid residues, 1-20 amino acid residues, 2-15 amino acid residues, 3-10 amino acid residues, 3-7 amino acid residues, 4-25 amino acid residues, 4-20 amino acid residues, 4-15 amino acid residues, 4-10 amino acid residues, 5-25 amino acid residues, 5-20 amino acid residues, 5-15 amino acid residues, or 5-10 amino acid residues. According to one embodiment, the linker comprises 1 to 5 units of the sequence of "GGP" (i.e., $(GGP)_{1-5}$); for example, the linker may comprise the amino acid sequence of "GGP", "GGPGGP" (SEQ ID NO: 9), "GGPGGPGGP" (SEQ ID NO: 10), "GGPGGPGGPGGP" (SEQ ID NO: 11), or "GGPGGPGGPGGPGGP" (SEQ ID NO: 12). According to another embodiment, the linker comprises 1 to 5 unit of the sequence of "GGGGS" (SEQ ID NO: 5); for example, the linker may comprise the amino acid sequence of "GGGGS" (SEQ ID NO: 5), "GGGGSGGGGS" (SEQ ID NO: 13), "GGGGSGGGGSGGGGS" (SEQ ID NO: 14), "GGGGSGGGGSGGGGSGGGGS" (SEQ ID NO: 15), or "GGGGSGGGGSGGGGSGGGGSGGGGS" (SEQ ID NO: 16). According to still another embodiment, the linker comprises the amino acid sequence of "EPKSS" (SEQ ID NO: 6). In one exemplary embodiment, the linker comprises the amino acid sequence of "GGGGSGGGGAS" (SEQ ID NO: 7).

Still optionally, the CLEC2.Fc protein further comprises a signal peptide (also known as "signal sequence") disposed at the N-terminus thereof. According to some embodiments of the present disclosure, the Fc region is disposed at and connected to the upstream of the extracellular domain of CLEC2; in these embodiments, the signal peptide is disposed at and connected to the upstream of the Fc region, i.e., the fusion protein comprises, from the N-terminus to the C-terminus, in sequence, a signal peptide, a Fc region, a linker (optionally) and an extracellular domain of CLEC2. According to alternative embodiments, the Fc region is disposed at and connected to the downstream of the extracellular domain of CLEC2; in these embodiments, the signal peptide is disposed at and connected to the upstream of the extracellular domain of CLEC2, i.e., the fusion protein comprises, from the N-terminus to the C-terminus, in sequence, a signal peptide, an extracellular domain of CLEC2, a linker (optionally) and a Fc region.

It is known that the signal peptide is a short peptide present at the N-terminus of a secretory protein or a membrane protein that mediates the protein targeting to the membrane of endoplasmic reticulum (ER). A skilled artisan may choose the signal peptide from an appropriate source in accordance with the desired purpose. For example, the signal peptide may be derived from interleukin-2 (IL-2), CD5, trypsinogen, serum albumin, IgG kappa light chain, or prolactin. According to one embodiment, the signal peptide of the CLEC2.Fc protein comprises the amino acid sequence of SEQ ID NO: 3. According to another embodiment, the signal peptide of the CLEC2.Fc protein comprises the amino acid sequence of SEQ ID NO: 4.

As an example, the amino acid sequence of the CLEC2.Fc protein is provided as SEQ ID NO: 8 below, in which the signal peptide (SEQ ID NO: 4) is underlined, the Fc region (SEQ ID NO: 2) is in italic font, the linker (SEQ ID NO: 7) is double underlined, and the extracellular domain of CLEC2 (SEQ ID NO: 1) is in boldface.

```
CLEC2.Fc protein
                                         (SEQ ID NO: 8)
MEWSWVFLFFLSVTTGVHSDKTHTCPPCPAPELLGGPSVFLFPPKPKD

TLMISRTPEVTCVVVDVSHEDPEVKFNWYVDGVEVHNAKTKPREEQYN

STYRVVSVLTVLHQDWLNGKEYKCKVSNKALPAPIEKTISKAKGQPRE

PQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSL

SLSPGKGGGGSGGGGASLGIWSVMQRNYLQGENENRTGTLQQLAKRFC
```

-continued

```
QYVVKQSELKGTFKGHKCSPCDTNWRYYGDSCYGFFRHNLTWEESKQY

CTDMNATLLKIDNRNIVEYIKARTHLIRWVGLSRQKSNEVWKWEDGSV

ISENMFEFLEDGKGNMNCAYFHNGKMHPTFCENKHYLMCERKAGMTKV

DQLP
```

In general, the CLEC2.Fc protein of the present disclosure may be produced by DNA technology, i.e., constructing a recombinant DNA encoding desired polypeptide sequences, followed by introducing the recombinant DNA into a host to express the polypeptide sequences. For example, the CLEC2.Fc protein of SEQ ID NO: 8 may be encoded by the polynucleotide of SEQ ID NO: 17.

(II-2) CLEC2 Vectors

In order to express the CLEC2 fusion protein provided herein, the appropriate coding sequences, e.g., SEQ ID NO: 17, can be cloned into a suitable vector. After introducing into a suitable host, the coding sequence can be expressed to produce desired polypeptide according to standard cloning and expression techniques, which are known in the art (e.g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989). The invention also relates to such vectors comprising a nucleic acid sequence according to the invention.

A "vector" refers to a delivery vehicle that (a) promotes the expression of a polypeptide-encoding nucleic acid sequence; (b) promotes the production of the polypeptide therefrom; (c) promotes the transfection/transformation of target cells therewith; (d) promotes the replication of the nucleic acid sequence; (e) promotes stability of the nucleic acid; (f) promotes detection of the nucleic acid and/or transformed/transfected cells; and/or (g) otherwise imparts advantageous biological and/or physiochemical function to the polypeptide-encoding nucleic acid. A vector can be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors.

A recombinant expression vector can be designed for expression of a CLEC2 fusion protein in prokaryotic (e.g., E. coli) or eukaryotic cells (e.g., insect cells, using baculovirus expression vectors, yeast cells, or mammalian cells). Representative host cells include those hosts typically used for cloning and expression, including Escherichia coli and mammalian cell lines. Alternatively, the recombinant expression vector can be transcribed and translated in vitro, for example using T7 promoter regulatory sequences and T7 polymerase and an in vitro translation system. Preferably, the vector contains a promoter upstream of the cloning site containing the nucleic acid sequence encoding the polypeptide. Examples of promoters, which can be switched on and off, include the lac promoter, the T7 promoter, the trc promoter, the tac promoter and the trp promoter.

Thus, provided herein are vectors comprising a nucleic acid sequence encoding CLEC2.Fc protein. In various embodiments, the vectors comprise an operably linked nucleotide sequence which regulates the expression of CLEC2.Fc protein. A vector can comprise or be associated with any suitable promoter, enhancer, and other expression-facilitating elements. Examples of such elements include strong expression promoters (e.g., a human CMV IE promoter/enhancer, an RSV promoter, SV40 promoter, SL3-3 promoter, MMTV promoter, or HIV LTR promoter, EF1alpha promoter, or CAG promoter), effective poly(A) termination sequences, an origin of replication for plasmid product in *E. coil*, an antibiotic resistance gene as a selectable marker, and/or a convenient cloning site (e.g., a polylinker). Vectors also can comprise an inducible promoter as opposed to a constitutive promoter such as CMV IE. In one aspect, a nucleic acid comprising a sequence encoding the CLEC2.Fc protein is operatively linked to a tissue specific promoter, which promotes expression of the sequence in a metabolically-relevant tissue, such as liver or pancreatic tissue is provided.

(II-3) Host Cells

In another aspect of the instant disclosure, host cells comprising the CLEC2.Fc nucleic acids and vectors disclosed herein are provided. In various embodiments, the vector or nucleic acid is integrated into the host cell genome, which in other embodiments the vector or nucleic acid is extra-chromosomal.

Recombinant cells, such as yeast, bacterial (e.g., *E. coli*), and mammalian cells (e.g., immortalized mammalian cells) comprising such a nucleic acid, vector, or combinations of either or both thereof are provided. In various embodiments, cells comprising a non-integrated nucleic acid, such as a plasmid, cosmid, phagemid, or linear expression element, which comprises a sequence coding for expression of the present CLEC2.Fc protein, are provided.

A vector comprising a nucleic acid sequence encoding the present CLEC2.Fc protein provided herein can be introduced into a host cell by transformation or by transfection. Methods of transforming a cell with an expression vector are well known.

The nucleic acid encoding the CLEC2.Fc protein can be delivered to a host cell or host animal via a viral vector. Any suitable viral vector can be used in this capacity. A viral vector can comprise any number of viral polynucleotides, alone or in combination with one or more viral proteins, which facilitate delivery, replication, and/or expression of the nucleic acid of the invention in a desired host cell. The viral vector can be a polynucleotide comprising all or part of a viral genome, a viral protein/nucleic acid conjugate, a virus-like particle (VLP), or an intact virus particle comprising viral nucleic acids and a CLEC2.Fc protein-encoding nucleic acid. A viral particle viral vector can comprise a wild-type viral particle or a modified viral particle. The viral vector can be a vector which requires the presence of another vector or wild-type virus for replication and/or expression (e.g., a viral vector can be a helper-dependent vim), such as an adenoviral vector amplicon. Typically, such viral vectors consist of a wild-type viral particle, or a viral particle modified in its protein and/or nucleic acid content to increase transgene capacity or aid in transfection and/or expression of the nucleic acid (examples of such vectors include the herpes virus/AAV amplicons). Typically, a viral vector is similar to and/or derived from a virus that normally infects humans. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors.

(II-4) Isolation of CLEC2.Fc Protein

The CLEC2.Fc protein expressed as described herein can be isolated using standard protein purification methods, e.g., affinity purification. Methods of purifying the CLEC2.Fc protein, as well as associated materials and reagents, are known in the art. Exemplary methods of purifying the CLEC2.Fc protein are provided in the Examples herein below. Additional purification methods that may be useful for purifying the CLEC2.Fc protein can be found in references such as Bootcov M R, 1997, Proc. Natl. Acad. Sci. USA 94:11514-9, Fairlie W D, 2000, Gene 254; 67-76.

(II-5) Methods of Treating SARS-CoV-2 Infection

The spike protein (S protein) is a large type I transmembrane protein found on coronaviruses (CoV) ranging from 1,160 amino acids for avian infectious bronchitis virus (IBV) and up to 1,400 amino acids for feline coronavirus (FCoV). In addition, this protein is highly glycosylated as it contains 21 to 35 N-glycosylation sites. Spike proteins assemble into trimers on the virion surface to form the distinctive "corona", or crown-like appearance. The ectodomain of all CoV spike proteins share the same organization in two domains: a N-terminal domain named S1 that is responsible for receptor binding and a C-terminal S2 domain responsible for fusion. SARS-CoV-2 spike protein has 1255 amino acids (SEQ ID NO: 18), with a 222 amino acid receptor binding domain (RBD; SEQ ID NO: 19) (amino acids 306-527 of SEQ ID NO: 18) and a 71 amino acid ACE2 binding motif (SEQ ID NO: 20) (amino acids 424-494 of SEQ ID NO: 18). It's been reported that 2019-nCoV (COVID-19) can infect the human respiratory epithelial cells through interaction with the human ACE2 receptor. Indeed, the recombinant spike protein can bind with recombinant ACE2 protein.

The inventor of the present disclosure unexpectedly discovers that CLEC2.Fc protein can complex with SARS-CoV-2 spike protein, and more specifically RBD, thereby inhibiting SARS-CoV-2 infection and SARS-CoV-2-induced NETosis.

Thus, another aspect of the present disclosure is directed to a method of treating SARS-CoV-2 infection by using the CLEC2.Fc protein in accordance with any embodiment of the present disclosure. The method comprises administering to the subject an effective amount of the present CLEC2.Fc protein thereby alleviating or ameliorating the symptom associated with SARS-CoV-2 infection.

According to some embodiments, the subject is a mouse, in which about 0.1 mg/kg to 100 mg/kg of the present CLEC2.Fc protein is administered to the subject; for example, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/kg. Preferably, about 0.5 mg/kg to 50 mg/kg of the present CLEC2.Fc protein is administered to the subject. More preferably, about 1 mg/kg to 10 mg/kg of the present CLEC2.Fc protein is administered to the subject. According to one working example, about 4 mg/kg to 5 mg/kg of the present CLEC2.Fc protein is sufficient to elicit a prophylactic effect in the subject (i.e., protecting the subject from SARS-CoV-2 infection). According to another working example, the administration of 8 mg/kg to 10 mg/kg of the present CLEC2.Fc protein elicits a therapeutic effect in the subject (i.e., alleviating or ameliorating the symptoms caused by SARS-CoV-2 infection).

A skilled artisan may readily determine the human equivalent dose (HED) of the present CLEC2.Fc protein, based on the doses determined from animal studies provided in working examples of this application. Accordingly, the effective amount of the present CLEC2.Fc protein suitable for use in a human subject may be in the range of 10 µg/kg to 10 mg/kg both weight for human; such as 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 µg/kg, or 1, 2, 3, 4, 5, 6, 7, 8, 9 or 10 mg/kg. Preferably, the HED is about 50 µg/kg to 5 mg/kg body weight; more preferably, about 0.1 mg/kg to 1 mg/kg body weight.

According to some embodiments of the present disclosure, the administration of CLEC2.Fc protein inhibits immunothrombosis, cell infiltration and collage deposition in lung.

The present method can be applied to the subject, alone or in combination with additional therapies that have some beneficial effects on the prevention or treatment of SARS-CoV-2 infection. Depending on the intended/therapeutic purpose, the present method can be applied to the subject before, during, or after the administration of the additional therapies.

(II-6) Methods of Treating Influenza Virus Infection

In addition to the prophylactic/therapeutic effect on SARS-CoV-2 infection, the inventor of the present disclosure also discovers that the CLEC2.Fc protein is useful in prophylactically treating influenza virus infection.

Accordingly, the present disclosure also provides a method of treating influenza virus infection by using the CLEC2.Fc protein. The method comprises administering to the subject an effective amount of the CLEC2.Fc protein in accordance with any embodiment of the present disclosure thereby alleviating or amelioraling the symptom associated with influenza virus infection.

According to some embodiments, the subject is a mouse, in which about 0.1 mg/kg to 100 mg/kg of the present CLEC2.Fc protein is administered to the subject; for example, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/kg. Preferably, about 0.5 mg/kg to 50 mg/kg of the present CLEC2.Fc protein is administered to the subject. More preferably, about 1 mg/kg to 10 mg/kg of the present CLEC2.Fc protein is administered to the subject. According to one working example, about 4 mg/kg to 5 mg/kg of the present CLEC2.Fc protein is sufficient to elicit a prophylactic effect in the subject (i.e., protecting the subject from influenza virus infection).

A skilled artisan may readily determine the human equivalent dose (HED) of the present CLEC2.Fc protein, based on the doses determined from animal studies provided in working examples of this application. Accordingly, the effective amount of the present CLEC2.Fc protein suitable for use in a human subject may be in the range of 10 µg/kg to 10 mg/kg body weight for human; such as 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 µg/kg, or 1, 2, 3, 4, 5, 6, 7, 8, 9 or 10 mg/kg. Preferably, the HED is about 50 µg/kg to 5 mg/kg body weight; more preferably, about 0.1 mg/kg to 1 mg/kg body weight.

According to certain embodiments of the present disclosure, the administration of CLEC2.Fc protein presents influenza virus-induced weight loss and lethality.

The influenza virus may be influenza type A virus (IAV) or influenza type B virus (IBV). According to some embodiments, the present CLEC2.Fc protein is useful in treating IAV infection and/or IAV infection-associated symptoms (e.g., weight loss), in which the IAV can be any of H1N1, H2N2, H3N2, H5N1, H7N7, H1N2, H9N2, H7N2, H7N3, H10N7 or H7N9. In one preferred example, the influenza virus is H5N1.

The present method can be applied to the subject, alone or in combination with additional therapies that have some beneficial effects on the prevention or treatment of influenza virus infection. Depending on the intended/therapeutic purpose, the present method can be applied to the subject before, during, or after the administration of the additional therapies.

Depending on desired purposes, the present CLEC2.Fc protein may be administered to the subject via a suitable route, such as subcutaneous, intratumoral, intradermal, intramuscular, intravenous, or intraperitoneal injection. According to preferred embodiments, the present CLEC2.Fc protein is intravenously administered to the subject.

The subject treatable with the present CLEC2.Fc protein and/or method is a mammal, for example, a human, a mouse, a rat, a monkey, a rabbit, a dog, a cat, a sheep, a goat, a horse, or a chimpanzee. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety,

EXAMPLE

Materials and Methods

Preparation of C-Type Lectin.Fc Proteins

Expi293F cells ($7.5 \times 10^7$) were seeded in 25.5 mL of medium ($2.9 \times 10^6$ cells/mL) in a 125-mL flask. 30 µg of plasmid DNAs encoding C-type lectin.Fc proteins (including CLEC5A.Fc protein, CLEC2.Fc protein, DC-SIGN.Fc protein, Dectin-1.Fc protein, Dectin-2.Fc protein and Mincle.Fc protein) were respectively diluted in 1.5 mL of OPTI-MEM® medium, followed by mixing gently. 81 µg of EXPIFECTAMINE™ 293 reagent was prepared into 1.5 mL of OPTI-MEM® medium, mixed well and then incubated at room temperature for 5 minutes. After the incubation, diluted plasmid DNA and diluted EXPIFECTAMINE™ 293 reagent were mixed to obtain a total of 3 mL of mixture. The mixture was incubated for 20 minutes at room temperature, and then added into the cells-containing medium. Cells were cultured at 37° C. and 8% $CO_2$ for 20 hours. Next. 150 µL of EXPIFECTAMINE™ 293 transfection enhancer 1 and 1.5 mL of EXPIFECTAMINE™ 293 transfection enhancer 2 were added to each flask. The supernatant was harvested at 24 hours post-add enhancers, and 60 mL of medium was used to resuspend the pellet followed by culturing for 48 hours, and harvesting the supernatant for antibody purification. Antibodies were purified using protein A column, and antibodies were concentrated by centrifugal filters.

Isolation of Human Neutrophils and Platelets

Whole blood was collected from drug-free healthy donors for the isolation of neutrophils and platelets. In brief, fresh blood was mixed with anticoagulant ACD (ratio 1:6, v/v), then centrifuged at 230×g for 15 minutes to collect platelet-rich plasma (PRP). Platelets were harvested by centrifugation at 1000×g for 10 minutes, then the pellet was suspended in Tyrode's buffer. For the isolation of neutrophils, blood was laid on the FICOLL-PAQUE® then centrifuged at 500×g for 15 minutes. Red blood cells (RRCs) were lysed with RBC lysis buffer and washed with saline. Neutrophils were suspended in Roswell Park Memorial Institute (RPMI) medium containing 10% autologous serum.

SARS-CoV-2 Prolongation

SARS-CoV-2 strain Taiwan/4/2020 was propagated in Vero E6 cells. Supernatant was stored at −80° C., and virus titer was determined by observation of the cytopathic effect (CPE) in Vero E6 cells.

Isolation of Extracellular Vesicles (EVs)

Plasma isolated from healthy donors and COVID-19 patients were centrifuged at 3,500×g for 15 minutes to remove cells and debris. The supernatant was further centrifuged at 100,000×g for 1.5 hour at 4° C. The pellet was washed with saline and then centrifuged at 100,000×g for 1.5 hour at 4° C. followed by suspending in 1 ml of saline. The protein concentration of EVs was measured by DC protein assay according to the manufacturer's instruction.

Induction of Neutrophils Extracellular Traps (NETs)

For SARS-CoV-2 stimulation, neutrophils ($4×10^5$) were stimulated with SARS-CoV-2 (MOI=0.1 or 1) and co-incubated with autologous platelets ($4×10^6$) for 5 or 20 hours at 37° C. For blocking assay with CLEC2.Fc protein, neutrophils ($4×10^5$) were stimulated with SARS-CoV-2 (MOI=0.1 or 1) at 37° C. in the presence of isotype control (hIgG1, 3 µg/ml) or CLEC2.Fc protein (3 µg/ml) with or without autologous platelets for 20 hours. For EVs stimulation, neutrophils were incubated with EVs from the plasma of healthy controls (HC-EVs) or EVs from COVID-19 patients for 3 hour at 37° C.

Visualization and Quantification of NET Structure

Samples were fixed with 4% paraformaldehyde and then permeabilized with 0.5% TRITON™ X-100 in phosphate buffered saline (PBS) for 15 minutes. Components of NETs were visualized by stain with anti-myeloperoxidase (MPO) antibody (1:100), anti-citrullinated histone antibody (1:100), and Hoechst 33342 (1:100,000). NETS histone area was captured by confocal microscope with white light laser system, and analyzed using software. The level of NET was calculated by area of histone (µm²).

Inhibition of SARS-CoV-2 Infection

Vero E6 cells transfected with human ACE2 were plated into 96-well plates for 16-24 hours. SARS-CoV-2 with or without serial dilution of CLEC2.Fc protein (10 µg/ml) or neutralizing antibody (RBD, 10 µg/ml) was incubated for 1 hour and then added to the wells. After 2 hours, DMEM containing 20% FBS and 2% penicillin-streptomycin was added to the cells followed by incubating at 37° C. for 48 hours. Plaque number was calculated and measured the neutralization (%).

Construction, Expression, and Purification of Recomobinant SARS-CoV-2 RBD Protein A DNA fragment encoding RBD domain of SARS-CoV-2 spike gene was amplified by reverse transcriptase-PCR and subcloned into pcDNA4/V5/His/A vector to generate SARS-CoV-2 RBD fusion protein. The His-tagged SARS-CoV-2 RBD fusion protein was overexpressed by using EXPI293™ expression system. Briefly, $7.5×10^7$ 293F cells in 25.5 ml of culture medium were transfected with a mixture of 30 µg of plasmid DNA and 81 µl of EXPI-FECTAMINE™ 293 reagent in a total of 3 ml of OPTI-MEM® I, followed by addition of EXPIFECTAMINE™ 293 transfection enhancer 1 and EXPIFECTAMINE™ 293 transfection enhancer 2 to the flask at 18-22 hour post-transfection. Culture supernatants were harvested at day 5 post-transfection, and the recombinant SARS-CoV-2 RBD was purified by column.

ELISA of C-Type Lectins-SARS-CoV-2 RBD Binding Assay

Wells coated with 50 µl of SARS-CoV-2 RBD (5 µg/ml in PBS) in each well (96 well ELISA plate) were stored at 4° C. overnight. Samples were washed once with PBST (PBS containing 0.05% of TWEEN®20) by microplate washer and then blocked with 100 µl of 3% bovine serum albumin (BSA) in PBST for 1 hour at room temperature. After washing, 50 µl of various recombinant human C-type lectin.Fc fusion proteins (50 µg/ml, 1% BSA in PBS) were added and incubated for 2 hours at room temperature. Plates were washed with PBST three times and incubated with 50 µl of HRP-conjugated anti-human IgG (H+L) antibody (1:10,000) for 1 hour at room temperature. HRP activity was revealed by the incubation of 100 µl TMB substrate (3,3', 5,5'-tetramethylbenzidine) for 15 minutes, and the reaction was then stopped by 50 µl of 2N $H_2SO_4$. The optical density at 450 nm was measured by absorbance microplate reader.

Measurement of Binding Affinity Between C-Type Lectin.Fc Fusion Proteins and SARS-CoV-2 RBD The binding affinity between C-type lectin-Fc fusion proteins and SARS-CoV-2 RBD was measured by biolayer interferometry. In brief, anti-penta-his (HIS1K) tips were soaked in PBS buffer and shaken on shaker for 20 minutes before they were used for the binding assay. All steps were performed at 30° C. with an agitation speed of 1,000 rpm on the flat bottom 96-well black plate. COVID-2019-Spike-328-585 (RBD) was immobilized at 20 µg/ml in PBS to HIS1K tips for 600 seconds to a response level of around 0.8 nm. Biosensor tips were then equilibrated for 60 seconds in PBS buffer before assessment of binding for 240 seconds followed by dissociation for 240 seconds. Human IgG1 and recombinant CLEC2.Fc protein, DC-SIGN.Fc protein and IgG1 were serially diluted two-fold in PBS (50 µM, 31 µM, and 8.8 µM). Biosensors were regenerated by three 5 second exposures to regeneration buffer (10 mM glycine pH 2.0) between each assay. Data analysis and curve fitting (1:1 binding model) was carried out with software. The measurement was performed in triplicate and shown as mean±s.d.

Mass Spectrum Analysis

EVs protein samples were lysed by lysis buffer containing phosphatase and protease inhibitors. Before the mass spectrometry analysis, samples were digested with trypsin then analyzed by mass spectrometer. Proteomics data was further analyzed by ingenuity pathways analysis (IPA).

Animal Study—SARS-CoV-2 Infection

C57BL/6 mice were inoculated with AAV-hACE2 at 14 days before the SARS-CoV-2 challenge. In the prophylactic model, mice were intravenously (i.v) injected with CLEC2.Fc protein (100 μg/mouse; about 4 mg/kg to 5 mg/kg); 1 hour later, the mice were intratracheally injected with SARS-CoV-2 ($8 \times 10^4$ PFU). In the therapeutic model, mice were intratracheally inoculated with SARS-CoV-2 ($8 \times 10^4$ PFU); 8 hours later, the mice were intraperitoneally (i.p) injected with CLEC2.Fc protein (200 μg/per mice; about 8 mg/kg to 10 mg/kg). Lung tissues were collected at 3 days and 5 days post-infection. The expression levels of cytokines and chemokines in lung tissues were respectively measured by quantitative PCR (qPCR), including inter- To address this question, recombinant C-type lectin.Fc proteins were immobilized on microtitration plates to capture SARS-CoV-2 RBD. It is found that CLEC2.Fc protein and DC-SIGN.Fc protein specifically interacted with SARS-CoV-2 RBD, while under the same conditions, CLEC5A.Fc protein, Dectin-1.Fc (CLEC7A) protein, Dectin-2.Fc (CLEC6A) protein, and Mincle.Fc (CLEC4F) protein did not interact with SARS-CoV-2 RBD (FIG. 1A). The binding affinities between SARS-CoV-2 RBD and C-type lectins were further measured by biolayer interferometry. The data of Table 1 indicated that the affinity between SARS-CoV-2 RBD and CLEC2.Fc protein was $7.92 \times 10^{-6}$ μM, which was higher than that between SARS-CoV-2 RBD and DC-SIGN.Fc protein ($18.7 \times 10^{-6}$ μM).

TABLE 1

| | | | | |
|---|---|---|---|---|
| Binding affinity between SARS-COV-2 RBD and specified C-type lectins | | | | |
| Binding affinity of SARS-COV-2-spike RBD and human C-type lectin.Fe fusion protein | | | | |
| | hIgG1 | hCLEC2.Fc | | hDC-SIGN.Fe |
| $K_{on}$ ($M^{-1}s^{-1}$) | N/A | $7.22 \times 10$ ($1.06 \times 10^2 \pm 3.67 \times 10$) | | $3.28 \times 10$ ($3.39 \times 10^2 \pm 1.04 \times 10$) |
| $K_{off}$ ($S^{-1}$) | N/A | $5.74 \times 10^{-4}$ ($8.49 \times 10^{-4} \pm 7.23 \times 10^{-4}$) | | $6.14 \times 10^{-4}$ ($5.88 \times 10^{-4} \pm 3.89 \times 10^{-4}$) |
| $K_0$ (M) | N/A | $7.92 \times 10^{-6}$ ($7.48 \times 10^{-6} \pm 4.26 \times 10^{-6}$) | | $18.7 \times 10^{-6}$ ($16.05 \times 10^{-6} \pm 7.25 \times 10^{-6}$) |

The binding affinity of SARS-COV-2-spike RBD and human C-type lectin. Fc protein was measured by Bio-layer interferometry (BLI).
$K_{on}$: rate constants for associated. $K_{off}$: rate constants for dissociation.
$K_D$: equilibrium dissociation constant.
Results were expressed as means ± s.d. from three independent experiments.

leukin (IL)-6, IL-10, tumor necrosis factor (TNF)-α, interferon (IFN)-γ, C-X-C motif chemokine ligand 1 (CXCL1), CXCL2, CXCL5, C-C motif chemokine ligand 2 (CCL2) and interferon gamma-induced protein 10 (IP10; also known as C-X-C motif chemokine ligand 10, CXCL10). The pulmonary pathology caused by SARS-CoV-2 was analyzed by immunohistochemistry (IHC) staining, in which the lung tissues isolated from the mice were stained with DAPI, anti-MPO antibody, anti-citrullinated histone H3 antibody, and anti-CD42b antibody. The MPO- and CD42b-positive areas were measured using software. Collagen deposits were stained with Picrosirius red. Collagen deposition was quantified using software and presented as area (μm²).

Animal Study—Influenza Virus Infection

C57BL/6 mice (male, 8 weeks old) were anesthetized, and then intranasally challenged with H5N1 (800 PFU/in 20 μl of saline). For prophylactic treatment, mice were intravenously injected with 100 μg/in 100 μl of isotype control (hIgG1, 100 μg/mouse) or CLEC2.Fc protein (100 μg/mouse; about 4 mg/kg to 5 mg/kg) before H5N1 inoculation Lung tissues were collected at 3 days post-infection, and the expression levels of viral protein, cytokines and chemokines in lung tissues were respectively measured by qPCR, including influenza M segment (influenza M), influenza matrix protein (influenza matrix), CXCL1, IP10, IL-1b, and IL-6. The weight and survival rate were monitored till day 21 post-infection.

Example 1 Effect of CLEC2.Fc Protein on SARS-CoV-2-Induced NET Formation

CLEC5A was previously demonstrated to be able to interact with dengue virus (DV). DC-SIGN has been reported to interact with spike protein of the severe SARS-CoV to enhance viral entry into ACE2-transfected cells. As SARS-CoV-2 RBD is responsible for the interaction with ACE2, whether SARS-CoV-2 RBD would interact with DC-SIGN and other Syk-coupled C-type lectins was investigated in this example.

As human CLEC2 is exclusively expressed on platelets, and DV activates platelets to enhance NET formation, whether platelets contribute to SARS-CoV-2-induced NET formation was further evaluated. At 5 hours post-incubation with SARS-CoV-2 (MOI=1), SARS-CoV-2 alone induced colocalization of citrullinated histone, chromosomal DNA and myeloperoxidase (MPO) within neutrophils, and these NETs were not released into the extracellular space (data not shown). In contrast, compared with the mock control group, robust aggregated NETs were observed in the presence of platelets (data not shown). The aggregated NET formation caused by SARS-CoV-2 was very different from the web-like NET structure induced by DV.

The level of SARS-CoV-2-induced NET formation increased with time, in which compared to the NET histone area observed at 5 hours post-incubation with infection SARS-CoV-2 (MOI=0.1), the NET histone area induced by SARS-CoV-2 obviously increased at 20 hours post-incubation in the presence or absence of platelets (data not shown). When the virus-neutrophil ratio further increases (MOI=1), virus alone induced NET formation as expected. Interestingly, NET formation attached to the culture plates decreased in the presence of platelets (data not shown), which can be explained by the NETs detaching from the culture plate, and only trace amounts of citrullinated histones and MPO were left in the culture plate (data not shown). Interestingly, in the absence of platelets, most NETs still adhered to the culture plate (data not shown).

Figure 1B:
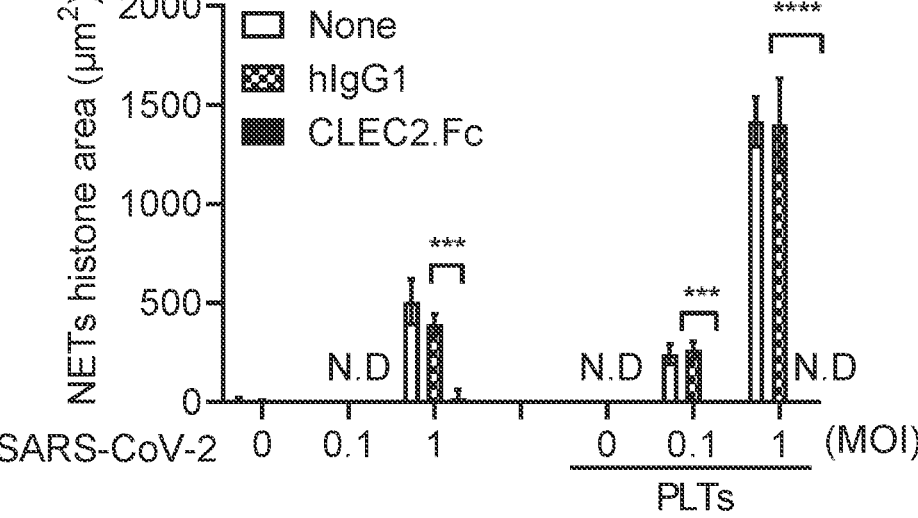

The data of FIG. 1B indicated that CLEC2.Fc not only inhibited SARS-CoV-2-induced NET formation, but also suppressed platelet-enhanced NETosis in vitro.

These data suggested that CLEC2 plays a critical role in SARS-CoV-2/platelet-induced NETosis, and the treatment of CLEC2.Fc protein is useful in inhibiting SARS-CoV-2-induced NET formation.

Example 2 Effect of CLEC2.Fc Protein on
SARS-CoV-2 Infection

The effects of CLEC2.Fc protein on inhibiting and treating SARS-CoV-2 infection were examined in this example. As described in Materials and Methods, in the prophylactic model, the CLEC2.Fc protein was given at 1 hour before SARS-CoV-2 challenge; while in the therapeutic model, the CLEC2.Fc protein was given 8 hours post-infection. Lung tissues were collected at 3 days and 5 days post-infection, followed by subjecting to qPCR analysis and IHC staining.

According to the results of qPCR, the administration of CLEC2.Fc protein significantly decreased the expression of proinflammatory cytokines (including IL-6, TNF-α, IFN-γ and IL-10), chemokines (including CXCL1, CXCL2, CXCL5, CCL2 and IP-10) at day 3 and day 5 post-infection. CLEC2.Fc protein after SARS-CoV-2 infection was still effective to reduce lung inflammation. CLEC2.Fc protein was still effective to inhibit the expression of IL-6, CXCL2, CXCL5, CCL2, and IP-10 at day 3 and day 5 post-infection, while the expression of TNF-α, IFN-γ, IL-10, and CXCL1 were suppressed at day 5 post-infection (data not shown).

Figure 2A:
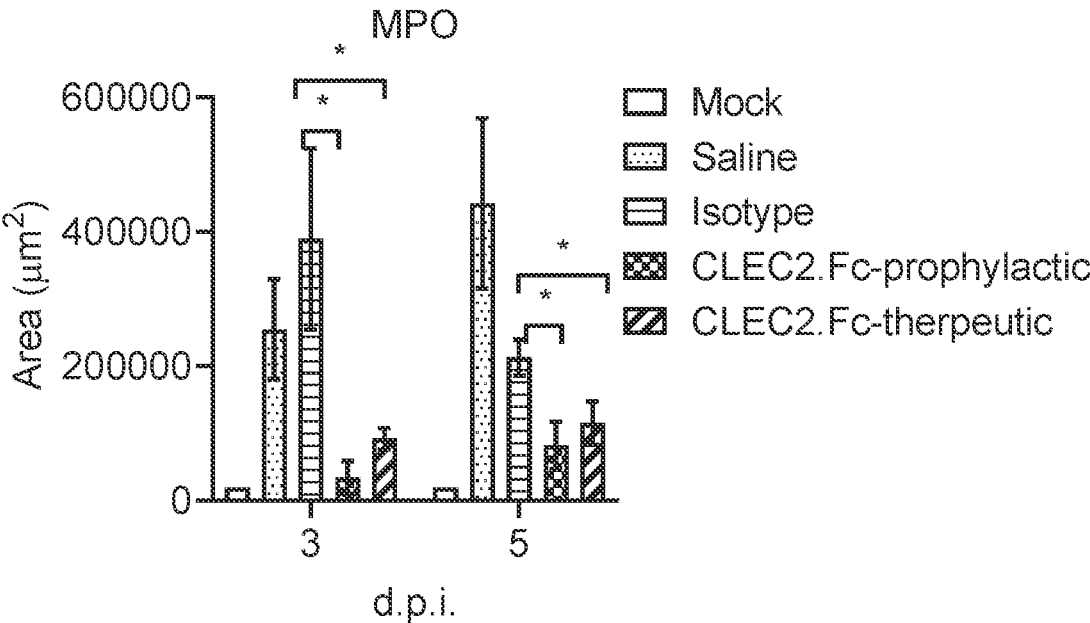
FIGS. 2A to 2C are histograms respectively depicting the prophylactic and therapeutic effects of CLEC2.Fc protein on SARS-CoV-2 infection according to Example 2 of the present disclosure.
Figure 2B:
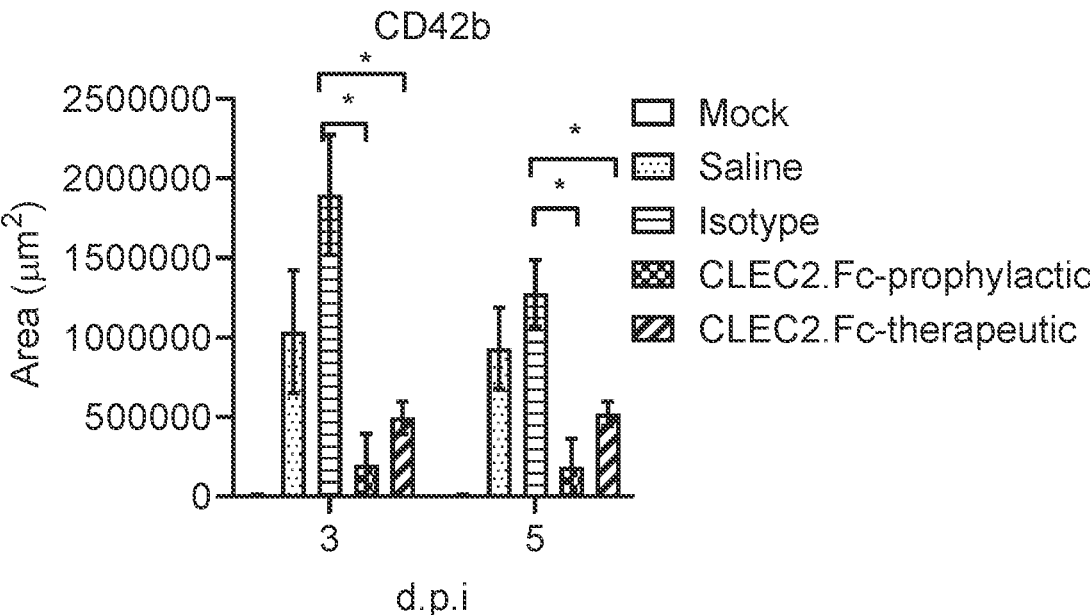
Figure 2C:
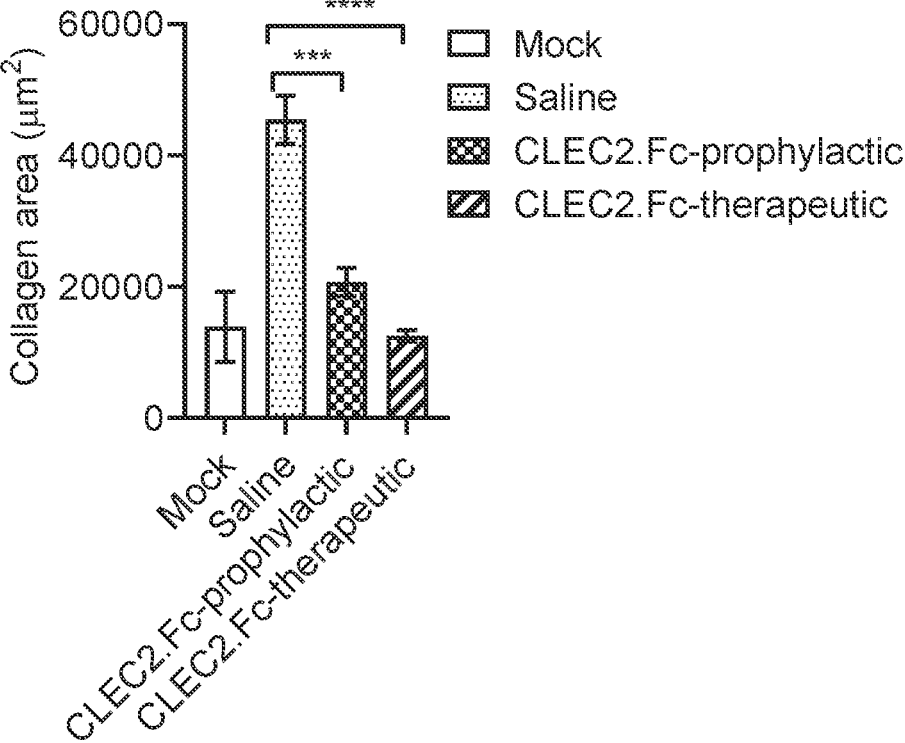

As the data depicted in FIGS. 2A to 2C, CLEC2.Fc protein efficiently suppressed NET, collagen upregulation and thrombus formations in vivo The data demonstrated that the present CLEC2.Fc protein provides a potential means to treat SARS-CoV-2 infection via downregulating the expression levels of inflammatory cytokines and chemokines, and inhibiting SARS-CoV-2-induced immunothrombosis, cell infiltration and collagen deposition in lung tissues.

Example 3 Protein Expression in COVID19-EVs

In this example, EVs were respectively isolated from the sera of COVID-19 patients and normal individuals, followed by subjecting to mass spectrometry analysis and IPA.

Figure 3:
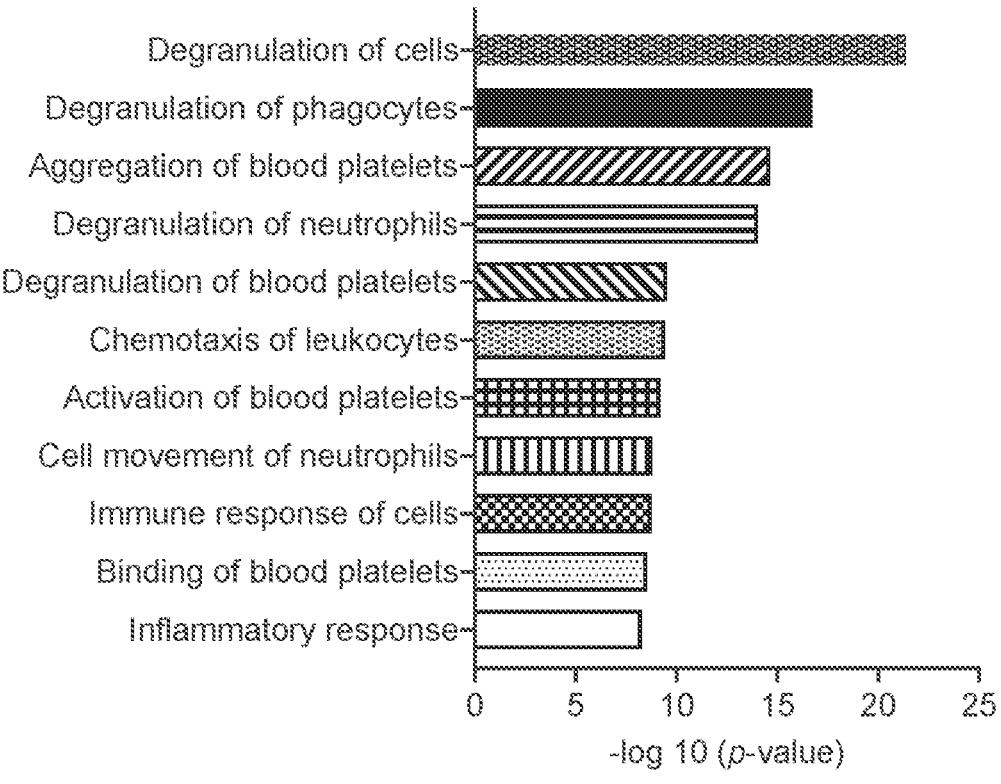
FIG. 3 depicts protein expression in COVID19-EVs according to Example 3 of the present disclosure. EVs from healthy controls (HCs-EVs, n=2) and COVID-19 patients (COVID19-EVs, n=3) were respectively harvested and analyzed by mass spectrometry. Proteins expressed in COVID-19 EVs, but not in HCs EVs, were further analyzed by ingenuity pathways analysis (IPA).

As the data depicted in FIG. 3 and Table 2, in COVID-19 patients' EVs, proteins involved in degranulation (including CD47, CD9, and platelet factor 4 (PF4)), platelet aggregation and activation (including CD9, and CLEC1B/CLEC2) were upregulated dramatically, but none of these proteins were detectable in EVs from healthy donors. As PF4 and CD47 are the specific platelet markers, this observation suggested that platelets are strongly activated in COVID-19 patients. Accordingly, EVs were further incubated with neutrophils to examine their ability to induce NET formation. Compared to the EVs from healthy controls, COVID-19-EVs induced robust NET formation in a dose-dependent manner (data not shown).

TABLE 2

| Expression of specified proteins in COVID19-EVs | | | |
|---|---|---|---|
| Diseases or Functions Annotation | Molecules | Number of molecules | −log 10 (p-value) |
| Degranulation of cells | ACTN4, ACTR2, ADAM10, ALAD, ANPEP, APP, CALM1, CCT8, CD226, CD47, CD84, CD9, CNN2, COTL1, CYB5R3, CYFIP1, DBNL, DDOST, EEF1A1, ENDOD1, GDI2, GPI, HPSE, HSP90AB1, IQGAP2, LYN, MMRN1, NCKAP1L, PEBP1, PF4, PGRMC1, PTPN6, RAB10, RAB27B, RAB5C, RALB, SELP, SERPINB1, STX11, SYTL4, TGFB1 | 41 | 21.55752 |
| Degranulation of phagocytes | ACTR2, ADAM10, ALAD, ANPEP, APP, CCT8, CD226, CD47, CD84, CD9, CNN2, COTL1, CYB5R3, CYFIP1, DBNL, DDOST, EEF1A1, GDI2, GPI, HPSE, HSP90AB1, IQGAP2, LYN, NCKAP1L, PEBP1, PF4, PGRMC1, PTPN6, RAB10, RAB5C, SERPINB1, STX11 | 32 | 16.71444 |
| Aggregation of blood platelets | ALOX12, ANXA7, APP, CD47, CD9, CLEC2, GNAQ, GNAZ, GP5, LYN, MPIG6B, MYLK, P4HB, PDIA4, PTPN6, RAB27B, SELP, TGFB1, TREML1, VASP | 20 | 14.64782 |
| Degranulation of neutrophils | ACTR2, ADAM10, ALAD, ANPEP, CCT8, CD47, CNN2, COTL1, CYB5R3, CYFIP1, DBNL, DDOST, EEF1A1, GDI2, GPI, HPSE, HSP90AB1, IQGAP2, NCKAP1L, PF4, PGRMC1, PTPN6, RAB10, RAB5C, SERPINB1, STX11 | 26 | 14.03905 |
| Degranulation of blood platelets | ACTN4, APP, CALM1 (includes others), CD9, ENDOD1, LYN, MMRN1, PF4, RAB27B, SELP, SYTL4, TGFB1 | 12 | 9.527244 |
| Chemotaxis of leukocytes | ADAM10, APP, CD47, CD9, DNM1L, GNAZ, HPSE, HSPD1, JAM3, LYN, MYLK, NCKAP1L, PF4, PLEC, PPIB, PRKCB, PTPN6, SELP, SERPINB1, TGFB1, TXN | 21 | 9.425969 |
| Activation of blood platelets | CLEC2, GNAQ, GNB1, GP1BB, GP5, LYN, MPIG6B, PF4, PRKCB, PTPN6, SELP, TREML1, VASP | 13 | 9.191789 |
| Cell movement of neutrophils | ADAM10, APP, CD47, CNN2, DNM1L, HSPB1, JAM3, LYN, MYLK, NCKAP1L, PF4, PRKCB, PTPN6, RTN4, SELP, SERPINB1, TGFB1, TXN, VASP | 19 | 8.793174 |
| Immune response of cells | ACTR2, ANPEP, ANXA11, APP, CALR, CD226, CD47, CLICA, CNN2, CORO1C, CYFIP1, DNM1L, EHD1, HSP90B1, HSPB1, IGHA2, KIF2A, LTBP1, LYN, NCKAP1L, PF4, PRKCB, PTPN6, RAB11A, RALB, TGFB1, VASP | 27 | 8.742321 |
| Binding of blood platelets | APP, CD226, CD84, CLEC2, FYB1, GP5, JAM3, PPIB, SELP, VASP | 10 | 8.542118 |

TABLE 2-continued

| | Expression of specified proteins in COVID19-EVs | | |
|---|---|---|---|
| Diseases or Functions Annotation | Molecules | Number of molecules | −log 10 (p-value) |
| Inflammatory response | ADAM10, APP, CD226, CD47, CD84, CD9, DNM1L, FKBP1A, GNAZ, GPX1, HPSE, HSPB1, HSPD1, JAM3, LTBP1, LYN, MAOB, MYLK, NCKAP1L, PF4, PLEC, PPIB, PRDX5, PRKCB, PTPN6, RALB, SELP, SERPINB1, TGFB1, TUBA1C, TXN | 31 | 8.271646 |

The mass spectrum analysis was performed using the LTQ Orbitrap XL mass spectrometer (Thermo Fisher Scientific Inc.) and the proteomics data were further analyzed by Ingenuity Pathways Analysis (IPA) software. The unique proteins present in EVs form COVID19 patients were listed in the table according to the result of IPA analysis.

Example 4 Molecular Modeling of CLEC2/SARS-CoV-2 RBD

According to the computational docking model of CLEC2 in complex with SARS-CoV-2 RBD, the residues of CLEC2 involved in SARS-CoV-2 RBD interaction were located in residues 151-157 and 186-191, while the residues of SARS-CoV-2 RBD involved in CLEC2 interaction were located in residues 444-450 and 479-500 (data not shown). To visualize CLEC2 bound to the trimeric SARS-CoV-2 spike glycoprotein, an artificial CLEC2 bound to the SARS-CoV-2 spike glycoprotein model was generated using CLEC2/SARS-CoV-2-RBD superimposed onto the RBD of the SARS-CoV-2 spike (data not shown). The RBD domain of the docking model was almost completely fitted to RBD of SARS-CoV-2 spike glycoprotein (data not shown). Therefore, in the absence of crystal structure of CLEC2/SARS-CoV-2 RBD, the docking model of CLEC2/SARS-CoV-2 RBD is reasonable.

The analytic results of crystal structures of SARS-CoV2-RBD and ACE2 indicated that ACE2 interacts with SARS-CoV2-RBD using 11 hydrogen bonds and 2 salt bridges. According to the SARS-CoV-2 RBD/CLEC2 modeling complex, CLEC2 interacted with SARS-CoV-2 RBD by 10 hydrogen bonds and 6 salt bridges (data not shown). Furthermore, ACE2 interacted with amino acid residues 446-456, 473-476, 484-489, and 493-505 of the SARS-CoV-2 RBD. Thus, the interaction of the domain of SARS-CoV-2 RBD with ACE2 was predicted to overlap with CLEC2.

Example 5 Effect of CLEC2.Fc Protein on Influenza Virus Infection

The effect of CLEC2.Fc protein on inhibiting influenza virus infection was examined in this example. As described in Materials and Methods, the CLEC2.Fc protein was intravenously administered to the mice before H5N1 inoculation. Lung tissues were collected at 3 days and 5 days post-infection, followed by subjecting to qPCR analysis. The weight and survival rate were monitored till day 21 post-infection.

Figure 4A:
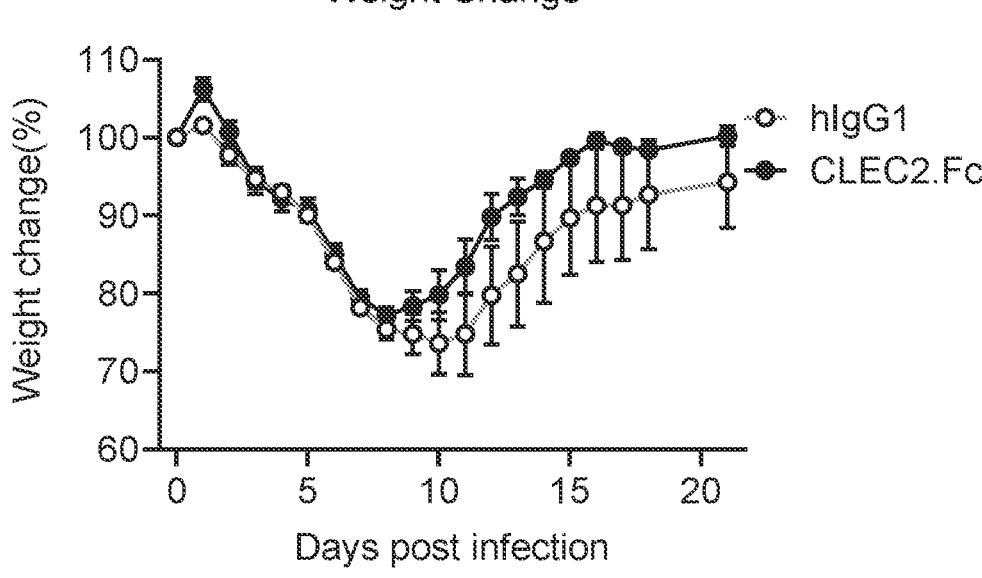
FIGS. 4A and 4B are line charts respectively depicting the prophylactic effect of CLEC2.Fc protein on SARS-CoV-2 infection according to Example 5 of the present disclosure.
Figure 4B:
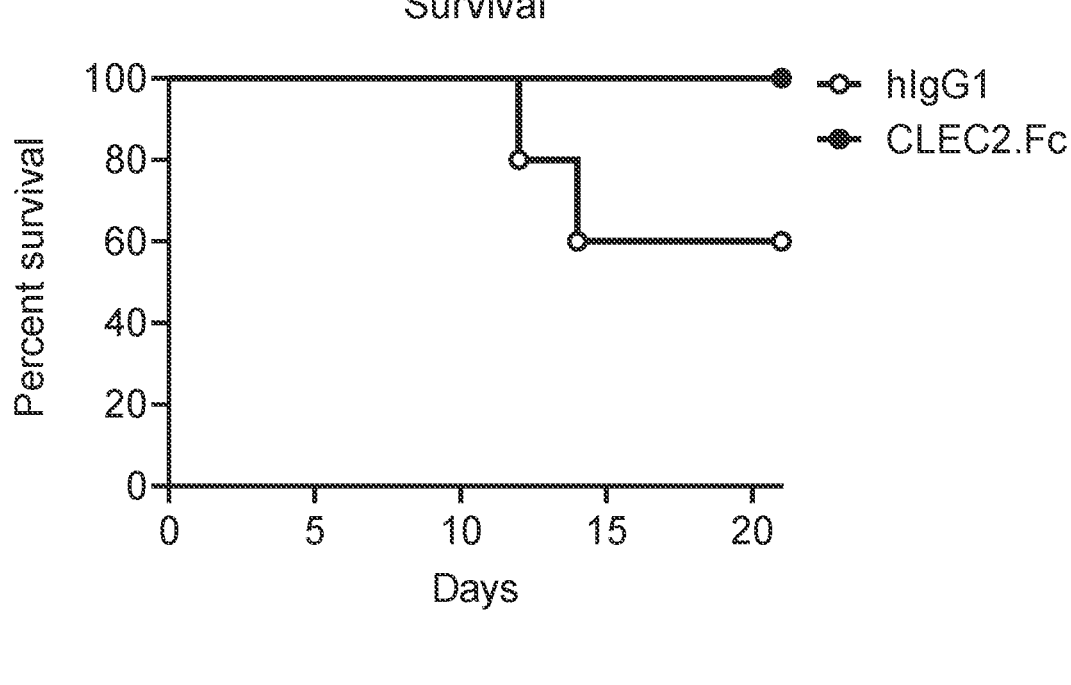

As the data depicted in FIGS. 4A and 4B, the administration of CLEC2.Fc protein prevented H5N1-induced weight loss (FIG. 4A) and lethality (FIG. 4B) in mice. Further, according to the results of qPCR, compared to the isotype control (hIgG), the treatment of CLEC2.Fc protein attenuated the expression levels of M gene and Matrix of H5N1 in lung tissues, and decreased the expression levels of H5N1-induced CXCL1, IP-10, IL-1β and IL-6 (data not shown).

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A fusion protein comprising an amino acid sequence of SEQ ID NO. 8.

2. A method of treating a subject with the infection of severe acute respiratory syndrome coronavirus 2 (SARS-COV-2), comprising administering to the subject an effective amount of the fusion protein of claim 1 thereby alleviating or ameliorating the symptom associated with SARS-COV-2 infection.

3. The method of claim 2, wherein the subject is a human, and the effective amount is 10 μg/kg to 10 mg/kg body weight of the subject.

4. The method of claim 3, wherein the effective amount is 0.1 mg/kg to 1 mg/kg body weight of the subject.

5. A method of treating a subject infected with influenza virus, comprising administering to the subject an effective amount of the fusion protein of claim 1 thereby alleviating or ameliorating the symptom associated with influenza virus infection.

6. The method of claim 5, wherein the subject is a human, and the effective amount is 10 μg/kg to 10 mg/kg body weight of the subject.

7. The method of claim 6, wherein the effective amount is 0.1 mg/kg to 1 mg/kg body weight of the subject.

* * * * *